United States Patent [19]

Di Renzo et al.

[11] Patent Number: 5,451,391
[45] Date of Patent: Sep. 19, 1995

[54] PROCESS FOR THE SYNTHESIS OF A CRYSTALLINE ALUMINOSILICATE ENRICHED IN SILICA, HAVING THE STRUCTURE OF MAZZITE, THE ALUMINOSILICATE OBTAINED AND ITS USE AS CATALYST FOR THE CONVERSION OF HYCROCARBONS

[75] Inventors: Francesco Di Renzo; Francois Fajula, both of Montpellier; Nisso Barbouth, Chatillon; Fredj Fitoussi, Lyons; Philippe Schulz, Ste Foix Les Lyon; Thierry des Courrieres, Lyons, all of France

[73] Assignee: Societe Nationale Elf Aquitaine, Courbevoie, France

[21] Appl. No.: 162,862

[22] Filed: Dec. 6, 1993

[30] Foreign Application Priority Data

Dec. 8, 1992 [FR] France ............................ 92 14774

[51] Int. Cl.⁶ ...................... C01B 39/34; B01J 29/70; C10G 47/04; C07C 4/06
[52] U.S. Cl. .................................... 423/702; 423/705; 423/714; 423/DIG. 26; 502/77; 502/85; 502/86; 208/111; 208/120; 208/134; 585/481; 585/533; 585/651; 585/653; 585/739
[58] Field of Search .............. 423/702, 704, 705, 712, 423/713, 714, 715, DIG. 26; 502/77, 85, 86; 208/134, 135, 113, 118, 120, 111; 585/481, 533, 651, 653, 739

[56] References Cited

U.S. PATENT DOCUMENTS

| | | | |
|---|---|---|---|
| 3,642,434 | 2/1972 | Dwyer et al. | 423/705 |
| 4,091,007 | 5/1978 | Dwyer et al. | 556/173 |
| 4,724,067 | 2/1988 | Raatz et al. | 502/85 |
| 4,780,436 | 10/1988 | Raatz et al. | 502/71 |
| 4,891,200 | 1/1990 | Fajula et al. | 423/705 |
| 5,139,761 | 8/1992 | Nair et al. | 423/713 |
| 5,157,198 | 10/1992 | Raatz et al. | 585/739 |
| 5,165,906 | 11/1992 | DiRenzo et al. | 423/718 |
| 5,230,790 | 7/1993 | Nair et al. | 585/467 |
| 5,277,791 | 1/1994 | DiRenzo et al. | 208/46 |
| 5,371,311 | 12/1994 | Nair et al. | 585/467 |

*Primary Examiner*—Mark L. Bell
*Assistant Examiner*—David Sample
*Attorney, Agent, or Firm*—Burgess, Ryan & Wayne

[57] ABSTRACT

Process for the preparation of a crystalline aluminosilicate enriched in silica, having the structure of mazzite, by hydrothermal crystallization of a gel containing sources of silicon, aluminum and alkali metal ions, in the presence of an organic structuring agent, characterized in that the source of aluminum is a zeolite Y in the form of spheres. The mazzite obtained does not contain any silicoalumina debris out of the lattice. It is employed as catalyst for the conversion of hydrocarbons or as molecular sieve.

19 Claims, 1 Drawing Sheet

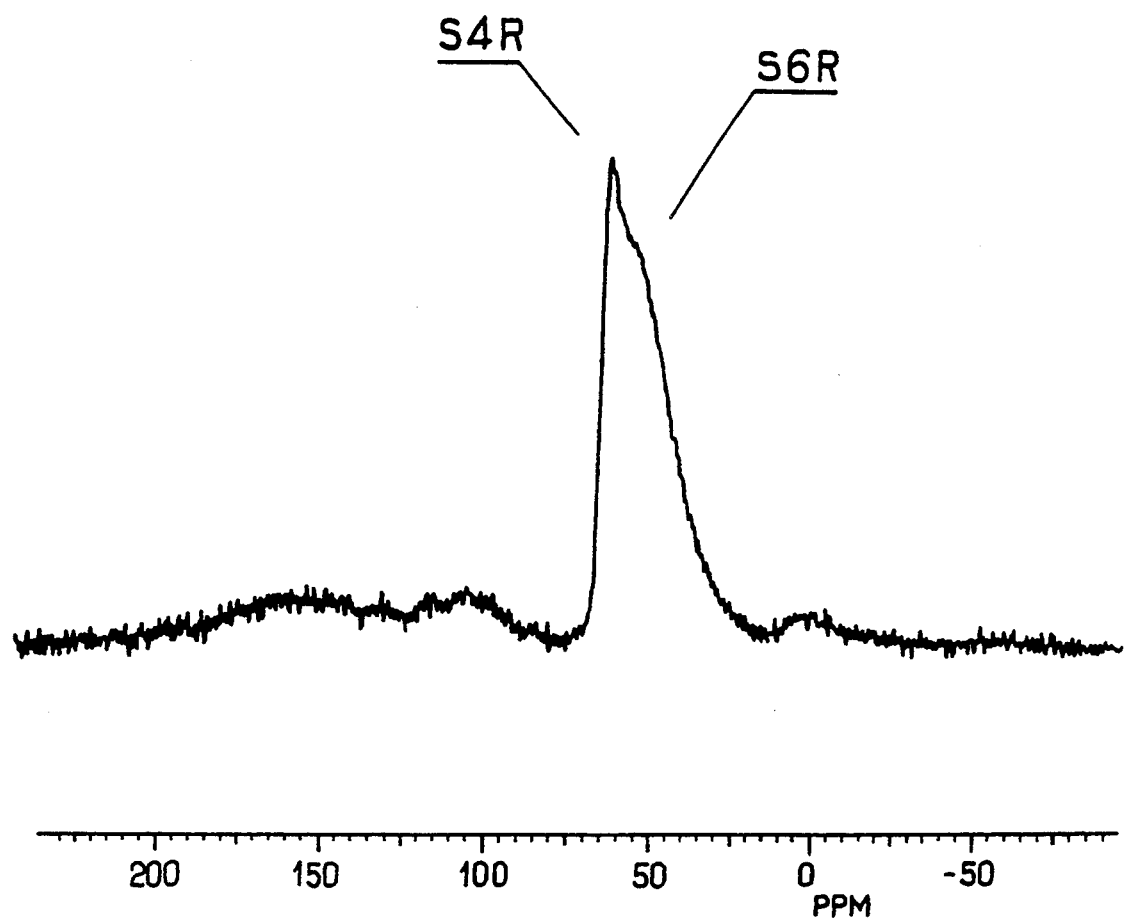

PROCESS FOR THE SYNTHESIS OF A CRYSTALLINE ALUMINOSILICATE ENRICHED IN SILICA, HAVING THE STRUCTURE OF MAZZITE, THE ALUMINOSILICATE OBTAINED AND ITS USE AS CATALYST FOR THE CONVERSION OF HYCROCARBONS

FIELD OF THE INVENTION

The present invention relates to the synthesis of a crystalline aluminosilicate enriched in silica, having the crystal structure of mazzite, to the aluminosilicate thus obtained and to its use as catalyst for the conversion of hydrocarbons.

RELATED ART

Obtained by a hydrothermal synthesis route for the first time in 1966 under the name of zeolite omega by Flanigen and Kellberg (U.S. Pat. No. 4,241,036), mazzite is a natural aluminosilicate identified in 1972 in the basaltic rocks of Mont Semiol, near Montbrison, Loire, France.

The structure of mazzite has been resolved by Galli (Cryst. Structure Comm. 3, 339, 1974) and Rinaldi et al. (Acta Cryst. B31, 1603, 1975). The structure, of hexagonal symmetry, results from the stacking of gmelinite cages (14-faced polyhedra) which share their faces consisting of rings with 6 tetrahedra along the crystallographic axis c. The columns of gmelinite cages are offset by c/2. The three-dimensional lattice which results from this assembly creates three systems of channels, all parallel to the c axis:

i) Quasicylindrical channels bounded by pores of 12 tetrahedra, whose free diameter is 0.74 nm (1 nm$=10^{-9}$m). The walls of these channels consist of infinite chains of rings of four and five tetrahedra and are therefore impenetrable to the majority of the usual molecules.

ii) Columns of gmelinite cages, to which access is very limited, through rings with 6 tetrahedra of free diameter of 0.28 nm.

iii) Channels consisting of the gaps between the columns of gmelinite cages, bounded by rings with 8 deformed tetrahedra with a free diameter of 0.34 nm.

Because of its structure, mazzite therefore belongs to the category of large-pored zeolites with unidirectional porosity. Its molecular sieve properties are described in a number of publications and patents (Flanigen, F. P. 1,548,382, Breck et al., Adv. Chem. Ser.. 121, 319, 1973, Ciric, F. P. 1,502,289, Perrotta et al., J. Catal. 55, 249, 1978, Chauvin et al., J. Catal. 11, 94, 1988).

Because of their large pore diameter and their high acidity, zeolites of the mazzite class have aroused keen interest for application in catalysis, such as cracking (Perrotta et al., J. Catal. 55,249,1978) and hydrocracking (Cole et al., Adv. Chem. Ser. 121, 583, 1973) of gas oils, alkylation (Bowes et al., U.S. Pat. No. 3,578,728, Flanigen et al., U.S. Pat. No. 4,241,036) and isomerization (Solinas et al., Appl. Catal. 5, 171, 1983) of aromatics, hydration of olefins (Fajula et al., J. Catal. 89, 64, 1984), the isomerization of light paraffins (Raatz et al., F. P. 2,657,869) and the hydroconversion of alkanes (Chauvin et al., Stud. Surf. Sci. Catal. 49B, 1397, 1989).

Numerous experimental procedures for the synthesis of zeolites of mazzite type are now known. Zeolites of this class (omega, ZSM-4, LZ 202, MZ-34) are prepared by hydrothermal reaction of alkali metal aluminosilicate gels between 90° and 150° C. The crystallization is generally performed in the presence of sodium cations and of an organic structuring agent such as, for example, tetramethylammonium or choline. One patent (Cannan U.S. Pat. No. 4,840,779) describes a synthesis of mazzite in the absence of organic agent, where the crystallization is initiated by the addition of zeolite seeds to the synthesis medium. In another example (Di Renzo et al., F. P. 2,651,221) the synthesis is performed in the presence of sodium, potassium and tetramethylammonium ions. The sources of silicon are those usually employed by a person skilled in the art, namely silica gels, colloidal silicas, precipitated silicas, silicates and hydrolysable silicic esters. Similarly, the sources of aluminium are those known in the art, such as aluminates, hydroxides, aluminas or amorphous and crystalline aluminosilicates. The use of natural or synthetic crystalline aluminosilicates in the synthesis of zeolites is especially employed for controlling the crystal growth through a slow and uniform of the source of aluminium. As a general rule, the source of crystalline aluminium employed is a material whose stability (solubility) in the synthesis medium is lower than that of the zeolite which it is intended to obtain. The growth of the desired zeolite entails the dissolving of the source of aluminium. Among the examples of crystallization of zeolites of mazzite type from aluminosilicates there may be mentioned syntheses starting from natural clays (Dwyer et al. U.S. Pat. No. 4,091,007, Fajula et al. U.S. Pat. No. 4,891,200) or from natural and synthetic zeolites of A, X, Y, ERI and MOR type (Dwyer U.S. Pat. No. 3,642,434, Plank, F. P. 2,027,390).

The conversion of a crystalline aluminosilicate phase into another one in hydrothermal conditions is a phenomenon which is well known to a person skilled in the art. This conversion may possibly take place without a source of crystalline reactant being deliberately introduced into the medium. It is not uncommon, in fact, for the appearance of the desired zeolite phase to be preceded by the transient formation of another phase, less stable in the medium (see, for example, R. M. Barrer, in "Hydrothermal Chemistry of zeolites", Academic Press, London, pp 174-176, 1982). These conversions conform to Ostwald's rule, which declares that, in a system where a number of polymorphs can form, the system changes towards the state which is thermodynamically the most stable by passing through the intermediacy of metastable states. The change of amorphous silica into cristobalite then into keatite and finally into quartz obeys this rule (Car et al., Amer. Mineral. 43, 908, 1958). In the case of zeolites the conversions amorphous >faujasite (Y) >gismondine (P), in the presence of sodium ions, and amorphous >faujasite (Y) >mazzite, in the presence of tetramethylammonium ions, are classical examples (Dwyer et al., J. Catal. 50,263, 1979, Fajula et al., Zeolites, 7, 203, 1987).

Regardless of the method of synthesis employed, the precursors of mazzite zeolite, that is to say the crude synthesis products, are obtained with Si/Al ratios of between 2.5 and 5 (that is, molar fractions of aluminium m=Al/(Al +Si) of 0.285 to 0,166). This high aluminium content, coupled with a unidirectional porosity, has unfortunate consequences for the applications in catalysis. On the one hand, during the thermal activation intended to decompose the organic agent trapped in the structure, a partial degradation of the structure takes place, resulting in the formation of amorphous residues remaining trapped in the pores. These residues obstruct the channels, and this leads to a severe blockage of the porosity. On the other hand, the high density of polar centres associated with the aluminium atoms promotes coking reactions during catalytic reactions, causing a rapid deactivation of the catalysts.

In order to overcome these disadvantages a controlled dealumination of the zeolite is generally performed before it is employed in catalysis. The purpose of this dealumination is to adapt the acidity of the zeolite to the requirements of the reaction. It is known that, for each zeolite and for each reaction catalysed thereby, the molar fraction of aluminium m plays a fundamental part. It determines directly the density and the strength of the acidic centres. Among the conventional methods of dealumination, those effected by isomorphous substitution of aluminium atoms with silicon atoms, for example treatments with ammonium hexafluorosilicate (Breck U.S. Pat. No. 4,503,023) or with silicon tetrachloride (Beyer et al., Stud. Surf. Sci. Catal. 24, 263, 1985) do not lead to satisfactory results in the case of structures with unidirectional porosity, because they produce a limited and irreproducible dealumination as a result of the diffusion constraints imposed by the structure. Furthermore, even in the cases where the dealumination is successfully performed using this route, the porosity of the zeolite is not modified by the treatment and no gain in stability of the catalytic activity is observed after dealumination (Chauvin et al., J. Catal. 126, 532, 1990).

A method of dealumination which permits at the same time an adjustment of the aluminium content of the lattice and the creation of a system of secondary pores which is beneficial to the diffusion of the reactants and products, while preserving the crystallinity, consists in performing a hydrothermal treatment of the zeolite followed by an acidic digestion, this second stage being intended to dissolve and remove the residues extracted from the zeolite framework. The literature provides a number of examples of dealumination of zeolites of mazzite type using this route (Raatz F. P. 2,584,385, Chauvin et al., Zeolites, 10, 174, 1990, Massiani et al., Appl. Catal. 42, 105, 1988). The hydrothermal treatment is performed at a temperature of between 400° and 800° C., either by purging the solid with a wet gas or by immersing the hydrated zeolite in a preheated furnace (known as steaming and self-steaming respectively). The acidic digestion is carried out in the presence of an aqueous solution of inorganic acid, at a concentration of between 0.01 and 10N at a temperature of between 20° and 150° C.

While the rate of extraction of the aluminium atoms from the zeolite lattice by a hydrothermal treatment can be controlled quite well by means of the operating conditions (water pressure, temperature, time), this is not so in the case of the acidic digestion. This difficulty is probably related to the fact that the reactions of polymerization or condensation of the aluminium-containing species extracted from the lattice and which occur inside the pores in the zeolite are not well controlled. The hydrothermal treatment thus results in the formation of species which are very different in chemical nature and size, and therefore in reactivity (solubility) towards the acid.

An excessively severe acidic digestion is accompanied by an additional dealumination of the lattice, or even by a partial dissolution of the latter, and by a loss of crystallinity that may go as far as a complete amorphization of the structure. Conversely, if the quantity of acid, the time or the reaction temperature are not sufficient, the final solid contains residues occluded in the pores which restrict the access of the reactants and contribute to the formation of coke during catalytic reactions. The conditions of the acidic digestion are therefore difficult to establish a priori because they themselves depend on the size of the crystals, the rate of the dealumination, the nature of the species out of lattice, the content of residual cations and, probably, other factors which have not yet been appreciated in the present state of knowledge. As a result, dealumination by a hydrothermal route and acidic digestion still remains empirical. The preparation of crystalline dealumized solids with an accessible porosity and free from aluminosilicate residues out of lattice requires a number of successive stages of cation exchange, of treatment with steam and of acidic digestion. The proliferation of these elementary stages makes an industrialization of this process for the dealumination of zeolites of mazzite type haphazard and, in any case, extremely costly.

BRIEF DESCRIPTION OF THE INVENTION

We have now found a simplified process which makes it possible to obtain, in a few stages, a crystalline aluminosilicate with a low molar fraction of aluminium and which has the structure of mazzite.

This aluminosilicate exhibits good activity and selectivity in acidic catalysis reactions and is characterized by an easily accessible porosity free from any aluminosilicate debris.

Our process for the preparation of a crystalline aluminosilicate enriched in silica, which has the structure of mazzite, comprises the following stages:
preparation of a crystallization gel containing at least one source of tetravalent silicon, of trivalent aluminium and of alkali metal ion, an organic structuring agent and water;
heating the gel to obtain the crystallization and then isolating, washing and drying the crystals;
heat treatment under wet atmosphere;
then digestion with an inorganic acid
and is characterized in that the source of trivalent aluminium consists of crystals of zeolite Y appearing in the form of spheres or botryoids.

The zeolite Y particles which are suitable for the process according to the invention are therefore bounded solely by rounded surfaces and not by planar faces.

BRIEF DESCRIPTION OF THE DRAWING

FIG. 1 is an $^{27}$Al NMR spectrum of the product of Example 1 which shows the presence of Al in the lattice only.

DETAILED DESCRIPTION OF THE INVENTION

Before the heat treatment under a wet atmosphere, called hydrothermal treatment, it may be advantageous to subject the dried crystals to a calcination at a sufficient temperature to decompose the organic structuring agent. After this calcination and before the hydrothermal treatment, the alkali metal ions present in the crystals can be exchanged for protons or ammonium ions.

The overall molar composition of the crystallization gel must preferably remain within the limits:
$SiO_2/Al_2O_3 = 20-200$
$SiO_2$/alkali metal ion $= 1.2-2$ structuring agent/alkali met al ion = 0.01–0.1
H₂O/alkali metal ion = 15–100

Sodium or a mixture of sodium and potassium is generally employed as alkali metal ion.

Among the organic structuring agents the tetraalkylammoniums are most commonly employed, and preferably tetramethylammonium.

The source of tetravalent silicon may be chosen from silicates, solid silicas, colloidal silicas, gels and dried gels, hydrolysable silicic esters or diatomites.

The zeolite of type Y, of appropriate morphology, is advantageously prepared by crystallization at 50° C. for ten days with stirring of an alkaline mixture of aluminosilicate of overall molar composition:

a Na₂O, Al₂O₃; b SiO₂, c H₂O where a is between 2 and 6, b between 5 and 15 and c between 100 and 200.

The alkalinity and the source of sodium are generally provided by sodium hydroxide. The source of silicon may be of the same origin as for the synthesis of the precursor of mazzite. The source of aluminium is generally an aluminium salt such as sodium aluminate or a reactive aluminium hydroxide. The crystals of zeolite Y are recovered by filtration or centrifuging, are washed with deionized water and are optionally dried in the oven between 50° and 100° C.

The precursor of mazzite is crystallized at a temperature of between 20° and 200° C., preferably between 100° and 150° C. at a pressure at least equal to the vapour pressure of the gel, for 4 to 96 hours and preferably from 10 to 50 hours.

The mazzite crystals are isolated from the reaction mixture by filtration or centrifuging, and are washed and dried in the oven between 50° and 100° C.

The calcination intended to decompose the organic agent occluded in the pores is performed under a flow of nitrogen or air or of a mixture of both gases. It consists in heating to a temperature higher than 450° C. for 5 minutes to 10 hours.

An aqueous solution of an ammonium salt or an inorganic or organic acid at a temperature of between 20 and 90° C. is employed for the exchange of the alkali metals. The residual weight content of sodium after exchange is generally lower than 1%.

The heat treatment under a wet atmosphere, called hydrothermal treatment, is performed at a temperature of between 450° and 850° C. under a wet atmosphere for a period of 1 minute to several hours. The parameters may be adjusted so as to obtain the Si/Al ratio aimed at in the three-dimensional zeolite lattice $(Si/Al)_R$.

An acid such as nitric acid, hydrochloric acid or sulphuric acid is generally employed for the digestion with the inorganic acid. A judicious choice of the acid concentration and of the treatment period and temperature enables the aluminosilicate debris to be removed quantitatively without affecting the crystallinity. In general the duration of the acidic digestion is between 10 minutes and 5 hours, the temperature between 20° and 100° C. and the acid concentration between 0.01 and 10N.

The aluminosilicate obtained exhibits an x-ray diffraction pattern characteristic of mazzite without continuous background that could reflect the presence of an amorphous phase. Its pore volume, measured by nitrogen adsorption at 77 K, is between 0.1 and 0.4 ml/g with from 5 to 50% of the latter contained in mesopores (pores with a diameter of between 2 and 50 nm). Its overall aluminium content, measured by elemental analysis, is identical with that of the zeolite framework. The aluminium content in the lattice can be easily measured by a person skilled in the art by virtue of the use of spectroscopic methods such as high resolution ²⁹Si NMR spectroscopy (see, for example, Engelhardt et al., "High-Resolution Solid-State NMR of Silicates and Zeolites", John Wiley and Sons, 1987), infrared spectroscopy or x-ray diffraction (B. Chauvin, thesis, Montpellier, 1988). However, the most direct method for demonstrating the presence of aluminosilicate residues out of lattice is high resolution ²⁷Al NMR spectroscopy. It is well known, in fact, that all the aluminium atoms of the zeolite framework have a uniform tetrahedral environment (Td) whereas the aluminium atoms associated with residues out of lattice, or silico-alumina debris, exhibit a coordination of 6 (octahedral symmetry) or, possibly, 5. Each of these coordinations of aluminium produces characteristic signals which are easily distinguishable in the high resolution ²⁷Al NMR spectra. Thus, the aluminium atoms in the lattice in a tetrahedral coordination give signals in the chemical shift regions of between 50 and 65 ppm (parts per million relative to a reference such as an aluminium salt or hydroxide in aqueous solution). The exact position and the number of the signals from the tetrahedral atoms depend on the number of nonequivalent crystallographic sites in the lattice. These are two in number in mazzite. The hexacoordinated (out of lattice) aluminium atoms give a signal between 5 and −5 ppm.

Finally, aluminium atoms in a coordination of 5 give a signal of between 20 and 40 ppm.

The crystalline aluminosilicates enriched in silica in accordance with the present invention have Si/Al ratios in the lattice $(Si/Al)_L$ and overall $(Si/Al)_o$ which are identical, higher than 10, and are characterized by high resolution ²⁷Al NMR spectra containing only the signals due to the tetracoordinated aluminium atoms in the crystalline lattice, and therefore included between 50 and 65 ppm.

Without wishing to be restricted by any theoretical consideration, we think that the complete elimination of the silicoalumina debris out of lattice during the acidic digestion is made possible by a particular distribution of the aluminium atoms in the precursor. During the hydrothermal treatment the species extracted from the lattice would appear to remain divided and therefore reactive and easily solubilizable by the acid.

The silica-enriched mazzite obtained can be employed as catalyst, pure, in the form of powder or particles. It may be advantageous to add to it an inert binder such as alumina, silica, silica-alumina or clays, particularly for the preparation of extrudates or beads.

The silica-enriched mazzite can also be employed in combination with other catalysts or active phases. The other catalysts may be zeolites, clays, metals or oxides, as a mechanical mixture or incorporated in the same binder as the mazzite. Among the active phases which may be added to the dealuminized mazzite there will be mentioned rare-earth cations, finely divided oxides or noble metals. In this case the additional active phase may be incorporated by any method known in the art, such as surface deposition, impregnation or cation exchange, performed either on the pure zeolite powder or on the processed zeolite.

The catalysts obtained can be employed, by themselves or in combination with other catalysts, for hydrocarbon conversion reactions such as the isomerization of alkanes, of olefins and of aromatics, the cracking and the hydrocracking of gas oils and of residues, the polymerization of light olefins for the synthesis of lubricants, or other conversion reactions of petroleum fractions.

The dealuminized mazzite is also useful for the conversion of organic substrates and as molecular sieve for drying and separation operations.

The following examples illustrate the invention without, however, limiting it.

EXAMPLE 1 a) A zeolite of type Y is prepared by crystallization, for 10 days at 50° C. with stirring, of a mixture of composition

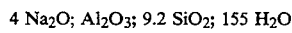
4 Na$_2$O; Al$_2$O$_3$; 9.2 SiO$_2$; 155 H$_2$O obtained from 28.4 grams of sodium hydroxide pellets, 320.1 g of water, 19.4 g of sodium aluminate (NaAlO$_2$) and 70.8 g of silica powder. The solid recovered (50 g), washed and dried, exhibits an x-ray diffraction pattern characteristic of zeolite Y. Its appearance, examined by electron scanning microscopy, is that of particles with a rounded surface from 0.2 to 0.5 μm in diameter. Its Si/Al ratio, determined by elemental analysis, is 2.7.

b) The precursor of mazzite is obtained by crystallization of a mixture

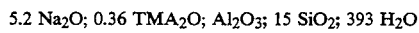
5.2 Na$_2$O; 0.36 TMA$_2$O; Al$_2$O$_3$; 15 SiO$_2$; 393 H$_2$O prepared as follows:

66.1 g of sodium hydroxide pellets and 14.2 g of tetramethylammonium chloride are dissolved in 1004.8 g of water. After the solution has cooled, 149.6 g of silica (silica gel, Cecagel from Ceca) are added with energetic stirring. After 10 minutes a suspension of 87.6 g of zeolite Y obtained in a) in 200 ml of water is added. The gel is kept stirred for two hours at ambient temperature and then transferred into a 2-l steel autoclave. The autoclave is heated to 115° C. and kept at this temperature for 24 hours with a stirring rate of the mixture of 150 revolutions per minute.

The crystals recovered by filtration, washed and dried in the oven at 110° C., produce an x-ray diffraction pattern characteristic of pure mazzite. Their size is from 1 to 1.5 μm in length by 0.5 to 0.7 μm in width (length over diameter equal to 2) with a uniform hexagonal prism habit. Elemental analysis results in an Si/Al ratio of 4 (aluminium fraction m=Al/(Al+Si)=0.20).

The precursor of mazzite was activated by:
calcining under a flow of air at 550° C. for 4 hours to decompose the organic agent,
exchange of the residual sodium ions with a 0.5N ammonium nitrate solution at 80° C.,
treatment in an atmosphere of steam at 620° C. for two hours,
acidic digestion for 4 hours at reflux temperature with a 1.5N solution of nitric acid and a volume of solution (ml)/weight of zeolite (g) ratio of 10.

At the end of the dealumination treatment the zeolite exhibits a crystallinity higher than 90% (determined by x-ray diffraction). Elemental analysis results in an Si/Al$_o$ ratio of 22 (m=0.043) and a residual sodium content lower than 0.05% by weight. Analyses by $^{29}$Si NMR and by infrared spectroscopy reveal an Si/Al$_L$ ratio of 22, that is identical with that found by elemental analysis. This result, which reflects the absence of aluminosilicate species occluded in the porosity was confirmed by NMR analysis of aluminium 27. The spectrum obtained, shown in FIG. 1, shows unambiguously that the only aluminium atoms present in the solid correspond to the atoms of the lattice in the two crystallographic sites (4-rings, signal at 61 ppm (S4L), and 6-rings, signal at 54 ppm (S6L)).

EXAMPLE 2

A zeolite of type Y is prepared by crystallizing at 50° C. for 12 days without stirring a mixture:

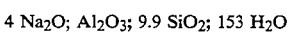
4 Na$_2$O; Al$_2$O$_3$; 9.9 SiO$_2$; 153 H$_2$O prepared from 160 g of water, 14.2 g of sodium hydroxide, 7 g of sodium aluminate and 35.5 g of solid silica.

This zeolite Y has an Si/Al ratio of 2.34 and Na/Al of 1. Its particles consist of aggregates of crystals of 0.25 μm average diameter.

The precursor of mazzite is synthesized in a 900-ml steel autoclave from a mixture

20.6 Na$_2$O; 1.2 TMA$_2$O; Al$_2$O$_3$; 60 SiO$_2$; 1455 H$_2$O prepared from 500 g of water, 31.45 g of sodium hydroxide, 81 g of silica gel (Cecagel) 18.68 g of zeolite Y and 9.05 g of tetramethylammonium hydroxide pentahydrate. This mixture is crystallized at 115° C. for 24 hours with stirring (300 revolutions/min). The solid recovered corresponds to pure mazzite which appears in the form of hexagonal crystals with an average size of 1.5×0.7 μm and an Si/Al ratio of 5.

One gram of this batch of mazzite was activated as indicated in example 1 except that the temperature of the hydrothermal treatment was 600° C. and the acid concentration 1N. The results of the characteristics of this solid after dealuminizing give a crystallinity of 95 %, an identical overall and lattice Si/Al ratio equal to 15 and a $^{27}$Al NMR spectrum containing only the signals at 60 ±2 and 54 ±2 ppm of the atoms of the zeolite lattice.

EXAMPLE 3

(Comparative)

The operating method of example 1 above was employed to prepare a precursor of mazzite by employing a commercial zeolite Y (NaY from ZEOCAT) with an Si/Al ratio of 2.7 and in which the crystals consist of polygonized particles (twinned crystals exposing faces with a low Miller index) from 0.4 to 1 μm in size.

After crystallizing for 24 hours at 115° C. with stirring, the solid obtained corresponds to a mixture of 43% of sodalite, 52% of analcime and only 5% of mazzite.

EXAMPLE 4

(Comparative)

A dealuminized mazzite was prepared from an aluminosilicate of high thermal stability, obtained according to example 5 of French Patent 2,582,234 (U.S. Pat. No. 4,891,200). The crystals obtained have a hexagonal habit from 3 to 4 μm in length by 0.3 to 0.7 μm in diameter and an Si/Al ratio of 3.2.

This precursor was subjected to the same dealuminizing treatment as that described in example 1 above. Elemental analysis of the solid produces an overall Si/Al ratio of 17, while measurements by $^{29}$Si NMR and infrared spectroscopy produce a lattice ratio equal to 22. The presence of aluminium out of lattice with a coordination of 6 (signal at 0 ppm) is clearly visible in the $^{27}$Al NMR spectrum. This example shows that, although the hydrothermal treatment has produced the same degree of extraction of the aluminium atoms from the zeolite lattice, the subsequent acidic digestion has not allowed the occluded species to be completely removed. A part of this sample was employed to prepare the catalysts B1 and B2 whose method of preparation and performance are described in examples 5 and 6 below. Another part was subjected to a new acidic digestion employing an acid concentration of 2N. This second acidic digestion resulted in a considerable degradation of the structure because the fraction collected had a crystallinity only 20 to 30% when compared with the original solid.

EXAMPLE 5

Preparation of catalysts A1 (zeolite dealuminized according to the procedure described in example 1, catalyst in accordance with the invention) and B1 (zeolite dealuminized according to the procedure described in example 4, comparative) and evaluation of their performance in the cracking of n-hexane.

The catalysts A1 and B1 are prepared by thermal activation of pure dealuminized zeolite, in powder form, at 550° C. under a flow of air. The n-hexane cracking reaction is performed at 350° C. at atmospheric pressure with an n-hexane flow rate of 1.5 ml/h and a pressure ratio p($N_2$)/P(n-$C_6$) of 6.2. The stream leaving the reactor is analysed at regular intervals in order to determine the activity of the catalyst and the stability of this activity as a function of the working period. The results recorded in table 1 below show that the catalysts in accordance with the invention (catalyst A1, dealuminized mazzite containing no silicoalumina debris) are more active and stable than the catalysts obtained by dealumination of mazzites obtained according to the methods of the prior art.

TABLE 1 conversion of n-hexane at 350° C. (expressed as percentage of moles of hydrocarbon which are cracked).

| Time under flow (min) | Conversions (%) | |
|---|---|---|
| | Catalyst A1 | Catalyst B1 (comparative) |
| 8 | 61.9 | 41.6 |
| 18 | 35.1 | 24.4 |
| 28 | 26.8 | 19.3 |
| 38 | 22.8 | 16.0 |
| 48 | 18.8 | 13.8 |
| 58 | 16.7 | 11.9 |
| 68 | 14.9 | 10.6 |

EXAMPLE 6

Preparation of a catalyst for hydroconversion of light paraffins in accordance with the invention (catalyst A2 prepared from the zeolite of example 1) and comparative example (catalyst B2 prepared from the zeolite of example 4).

The dealuminized zeolite is blended with alumina and water to form a pasty mixture containing 20% by weight of alumina. This mixture is extruded through a die and is dried and calcined. The extrudates obtained have a diameter of 1.6 mm and a length of between 3 and 5 mm.

The deposition of platinum on the catalyst is performed by cation exchange with the salt Pt(NH$_3$)$_4$Cl$_2$.H$_2$O, in the presence of a competing ion (ammonium nitrate). The weight content of platinum in catalysts A2 and B2 is 0.3%.

The catalyst is then activated by first of all performing a calcination under air at 520° C. and then a reduction of the metal under a stream of hydrogen, the temperature being gradually raised from 150° to 450° C.

This procedure results in metal phases which are perfectly divided and distributed within the solid.

The activity of the catalysts is determined in a stationary-bed catalyst unit, between 150° and 300° C., under 1 atmosphere of total pressure, an H$_2$/n-C$_6$ molar ratio of 70 and a space velocity, expressed as the ratio of the masses of feedstock and catalyst, of 0.2 h$^{-1}$.

The performance of the catalysts is defined from the following criteria:

i) The temperature (T$_{50\%}$ in ° C.) necessary to obtain a 50% conversion of n-hexane. The conversion is defined as: (mass of n-hexane in the feedstock—mass of n-hexane in the delivery/mass of n-hexane in the feedstock)×100.

ii) The yields of dibranched isomers (in %) at 50% conversion: 2,3-dimethyl butane (23DMB) and 2,2-dimethyl butane (22DMB). The yield is calculated as: (mass of the hydrocarbon in question/total mass of the hydrocarbons in the delivery)×100.

iii) The temperature of appearance of the cracking products (T$_{crack}$ in ° C.).

iv) The optimum conversion and the temperature at which this conversion is reached (%$_{max}$ at T° C.).

The results of the evaluation of the two catalysts are given in table 2 below.

TABLE 2

Evaluation of the performance of catalysts A2 and B2 for the hydroisomerization of an n-hexane feedstock:

| Catalyst | T$_{50\%}$ (°C.) | Yield (%) | | T$_{crack}$ (°C.) | %$_{max}$ at T °C. | |
|---|---|---|---|---|---|---|
| | | 22DMB | 23DMB | | | |
| A2 | 190 | 5.2 | 8.02 | 232 | 85 | 245 |
| B2 | 200 | 4.9 | 7.32 | 231 | 86 | 255 |

The data in table 2 show that catalyst A2, in accordance with the invention, is more active (lower operating temperatures T$_{50\%}$ and %$_{max}$ at T° C. to obtain the same degree of conversion of n-hexane (points i and iii)) but above all more selective for dibranched isomers (point ii) than the catalyst of reference B2, prepared according to the prior methods of the art.

We claim:

1. In a process for preparation of a crystalline aluminosilicate enriched in silica, which has the structure of mazzite, comprising
   (a) preparing a crystallization gel containing a source of tetravalent silicon, of trivalent aluminum and of alkali metal ion, an organic structuring agent and water;
   (b) heating the gel to obtain crystallization and isolating, washing and drying the crystals;
   (c) heat treating the crystals to a heat treatment under a wet atmosphere; and
   (d) digesting the crystals with an inorganic acid; the improvement which comprises: the source of trivalent aluminum consists of crystals of zeolite Y in the form of spheres or botryoids.

2. The process according to claim 1, wherein, the crystallization gel comprises:
   (a) SiO$_2$/Al$_2$O$_3$=20–200;

(b) SiO$_2$/alkali metal ion = 1.2-2;
(c) structuring agent/alkali metal ion = 0.01-0.1
(d) H$_2$O/alkali metal ion = 15-100

3. The process of claim 1, wherein before the heat treatment under a wet atmosphere the crystals are subjected to a calcination at a temperature which is sufficient to decompose the organic structuring agent.

4. The process of claim 3, wherein the calcination is performed for 5 minutes to 10 hours, at a temperature higher than 450° C. under a flow of nitrogen, air or mixtures thereof.

5. The process according to claim 1 wherein before the heat treatment under a wet atmosphere, the alkali metal cations present in the crystals are exchanged with protons or ammonium ions.

6. The process of claim 5, wherein the alkali metal cations are exchanged with an aqueous solution of an ammonium salt or an inorganic or organic acid.

7. The process according to claim 1 wherein the source of tetravalent silicon is at least one member selected from the group consisting of silicates, solid silicas, colloidal silicas, gels, dried gels, hydrolysable silicic esters and diatomites.

8. The process according to claim 1, wherein the alkali metal ion comprises sodium or a mixture of sodium and potassium.

9. The process of claim 1, wherein the organic structuring agent is a tetraalkylammonium.

10. The process of claims 9 wherein the crystals are digested with an acid selected from the group consisting of nitric acid, hydrochloric acid and sulphuric acid.

11. The process of claim 10, wherein the duration of the acidic digestion is between 10 minutes and 5 hours, at a temperature between 20° and 100° C. and an acid concentration between 0.01 and 10N.

12. The process of claim 1 wherein the crystallization gel is heated to a temperature of between 20° and 200° C., at a pressure at least equal to the vapour pressure of the gel for 4 to 96 hours.

13. The process of claim 12, wherein the crystalline gel is heated at a temperature of from 100° C. to 150° C.

14. The process of claim 13, wherein the crystallization gel is heated for from 10 to 50 hours.

15. The process of claim 1 wherein the heat treatment under a wet atmosphere is performed at a temperature of between 450° and 850° C. for a period of 1 minute to about 2 hours.

16. The process of claim 1 wherein the zeolite Y in the form of spheres is prepared by hydrothermal crystallization of a mixture containing a source of tetravalent silicon, a source of trivalent aluminium, sodium hydroxide and water according to the proportions:

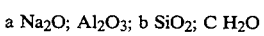

where a is between 2 and 6, b is between 5 and 15 and C is between 100 and 200.

17. A crystalline aluminosilicate enriched in silica obtained by the process of claim 1 wherein the crystalline aluminosilicate has an identical lattice and overall silicon/aluminum ratios which are higher than 10 and have high-resolution $^{27}$Al NMR spectra in which the aluminum provides only signals between 50 and 65 ppm.

18. A hydrocarbon conversion catalyst which comprises the aluminosilicate of claim 17.

19. In a catalytic hydrocarbon conversion process selected from the group consisting of isomerization of alkanes, isomerization of olefins, isomerization of aromatics, cracking, hydrocracking and polymerization of olefins the improvement which comprises using as the catalyst, the catalyst of claim 18.

* * * * *